United States Patent [19]

Leishman

[11] Patent Number: 5,036,852
[45] Date of Patent: Aug. 6, 1991

[54] MEDICAL EQUIPMENT MONITOR APPARATUS AND METHOD

[76] Inventor: Mark L. Leishman, 248 E. 470 North, Bountiful, Utah 84010

[21] Appl. No.: 447,913

[22] Filed: Dec. 8, 1989

[51] Int. Cl.[5] .............................................. A61B 5/00
[52] U.S. Cl. .................................. 128/630; 128/904; 379/38
[58] Field of Search ............... 128/633, 630, 721, 904; 379/38

[56] References Cited

U.S. PATENT DOCUMENTS

| | | | |
|---|---|---|---|
| 4,259,548 | 3/1981 | Fahey et al. | 379/38 |
| 4,838,275 | 6/1989 | Lee | 128/904 |
| 4,890,621 | 1/1990 | Hakky | 128/635 |

Primary Examiner—Kyle L. Howell
Assistant Examiner—Kevin Pontius
Attorney, Agent, or Firm—J. Winslow Young

[57] ABSTRACT

A medical equipment monitor apparatus and method whereby the normal operating conditions and alarm situations for the medical equipment are intercepted by the monitor where they are recorded and selectively transmitted to a base computer system at a remote location. Importantly, alarm conditions of the medical equipment are promptly transmitted over a telephone to the base computer to alert the operating personnel to the alarm condition. The monitor system also provides for a printed copy to be produced from selected data provided to the base computer by the monitor apparatus.

18 Claims, 6 Drawing Sheets

MEDICAL EQUIPMENT MONITOR APPARATUS AND METHOD

BACKGROUND

1. Field of the Invention

This invention relates to monitors and, more particularly, to a novel medical equipment monitor apparatus and method whereby remotely located medical equipment is continuously monitored for selected performance characteristics.

2. The Prior Art

Advances in modern healthcare, particularly the rapid technological advances being experienced almost daily in the healthcare industry, represent significant benefits to patients through improved healthcare delivery to the patient. However, these advances are accompanied by increased costs to society. Not only do these remarkable technological advances contribute to the overall cost increases in healthcare services but they also extend the period over which these costs are incurred by extending the lifespan of persons who would have otherwise died. An important aspect of the foregoing is the recent trend to move patients out of the hospital setting into less costly environments such as skilled nursing facilities in certain instances although the preferred environment is that of the home setting.

Healthcare delivery in the home on an outpatient basis not only reduces the overhead and labor costs for facilities and skilled nursing care but also places the patient in familiar surroundings in the presence of others who are emotionally attached to the patient. It is a well-known phenomena that a patient in familiar surroundings and in the presence of loved ones experiences a remarkably increased feeling of well being and a more rapid recovery. Accordingly, there is an increasing interest in moving patients, whose conditions only a decade or so ago would have mandated hospitalization, out of the hospital setting into, preferably, the home setting.

This outplacement of patients means that certain items of fairly sophisticated life support equipment must accompany the patient to the home setting. One common item of life support equipment, for example, is an oxygen delivery system that can include a source of either compressed or liquid oxygen or derive its oxygen from an oxygen concentrator. Accompanying this piece of equipment is a pulse oximeter for measuring the oxygen concentration in the blood of the patient as well as an apnea monitor, in certain instances. The equipment is generally leased and maintained by a home healthcare agency that is responsible for its proper operation.

However, in the absence of a skilled professional such as found in the hospital setting, there is no apparatus or method for continuously monitoring this equipment on a twenty-four hour basis. The home healthcare agency does send a technician into the home on a regular basis of three or four times a week, but there is no accurate monitoring of this equipment on a consistent basis. Further, equipment failure may either go unrecognized by the patient and those around him or her or be of such a nature that the reporting person may erroneously report the wrong system malfunction. It is also a well-known problem that certain equipment undergoes a gradual deterioration in its performance during use so that the loss of support to the patient is especially insidious over time.

In view of the foregoing what is needed is a medical equipment monitor apparatus and method for directly and continuously monitoring the performance of selected items of medical equipment not only to provide an appropriate alarm signal but also to record all desired parameters of the operational characteristics of the equipment. It would also be a significant advancement in the art to provide the medical equipment monitor apparatus with the capability to transmit information and alarm conditions to a remote location. Such a novel apparatus and method is disclosed and claimed herein.

BRIEF SUMMARY AND OBJECTS OF THE INVENTION

This invention relates to a novel, medical equipment monitor apparatus and method whereby selected medical equipment is electronically monitored to determine its performance characteristics. The monitor is a simple computer system dedicated to monitoring one or more selected items of medical equipment. The monitor apparatus not only records the monitored parameters but also provides an alarm signal for preprogrammed alarm conditions. The monitor apparatus also has the capability to transmit this information to a preselected remote location. The items of selected medical equipment receive electrical power directly through the monitor and are also electronically coupled directly to the computer portion of the monitor so as to enable the monitor to accurately determine the operation and any alarm conditions of the medical equipment. The monitor is coupled with a telephone line so as to provide a communication link between the monitor and a central station for transmitting information about the medical equipment as well as any alarm conditions.

It is, therefore, a primary object of this invention to provide improvements in medical equipment monitors.

Another primary object of this invention is to provide improvements in the method of monitoring medical equipment.

Another object of this invention is to provide an individually programmable monitor for monitoring the operational characteristics of one or more items of medical equipment.

Another object of this invention is to provide an alarm system in the monitor so as to produce an alarm signal when the operation of the medical equipment deviates beyond the programmed limits for the medical equipment.

Another object of this invention is to provide a monitor for medical equipment whereby the monitor electronically records and transmits to a remote location over a telephone line the operational and alarm conditions of the medical equipment.

These and other objects and features of the present invention will become more readily apparent from the following description in which preferred and other embodiments of the invention have been set forth in conjunction with the accompanying drawing and appended claims.

DETAILED DESCRIPTION OF THE PREFERRED EMBODIMENT

General Discussion

Figure 1:
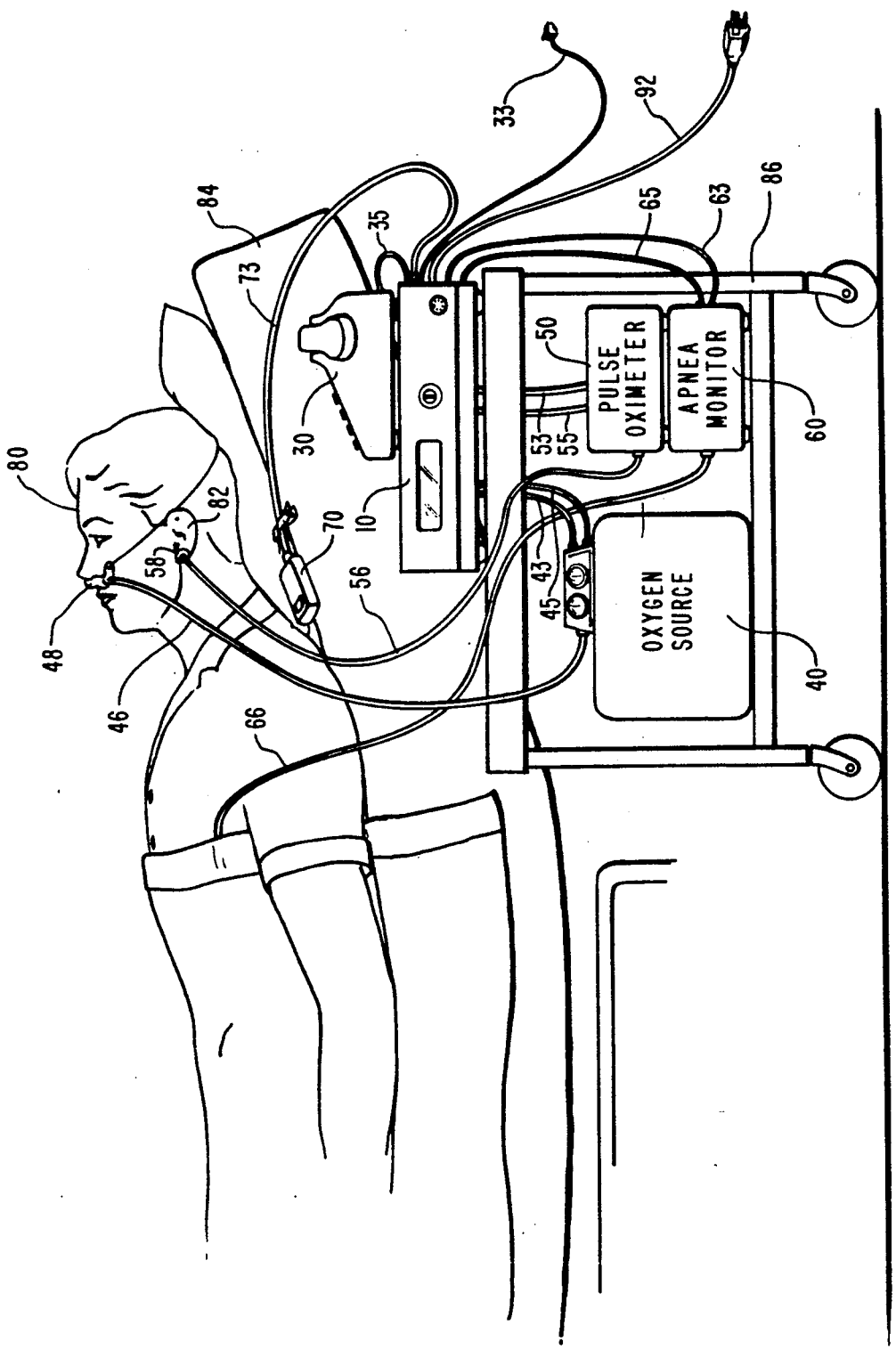
FIG. 1 is a frontal view of the novel monitor apparatus of this invention shown in the environment of selected items of medical equipment and a patient being serviced by the medical equipment.

As a rule, any patient in the intensive care portion of a hospital is coupled directly to one or more monitors for the purpose of enabling the healthcare professionals to quickly and accurately determine certain parameters of the patient such as heart rate, oxygen saturation, pulse, and the like. Historically, these parameters are monitored for certain, predetermined alarm conditions and are also recorded so as to become a portion of the patient's permanent record. This type of monitor is well known in the art and is used extensively throughout the healthcare industry.

However, this foregoing monitor system, in effect, interfaces the patient between the medical equipment and the monitor so that if an alarm condition is encountered it is not immediately clear whether the alarm condition is directly patient related or is a secondary effect produced by failure of the medical equipment. For example, if a blood oximeter detects a lowering of the blood oxygen concentration the question is whether this signal is a result of respiratory distress unrelated to the supply of oxygen to the patient or the direct result of a failure in the oxygen supply. Accordingly, it is important for the healthcare professional to be able to determine rapidly when a potentially hazardous medical condition is determined in order to take prompt remedial action.

The present invention is designed specifically to monitor the medical equipment directly to determine its operational characteristics within certain, predetermined parameters. Operational characteristics outside these parameters are sensed as an alarm condition and this alarm condition is automatically transmitted over a telephone line to a remote location.

Illustrative of the need for this type of monitoring capability is the well-known fact that commercially available, oxygen concentrator equipment undergoes a gradual degradation in its performance characteristics over time. In particular, the inlet filter beds of the oxygen concentrator become occluded with dust during operation so that there is a long term decline in the percentage of oxygen delivered to the patient. Regrettably, this decline is so slow that no perceptible change is apparent in the patient until the patient is in noticeable distress. Unfortunately, the oxygen concentrator continues to deliver a flow of what appears to be oxygen-enriched gas but that is essentially room air with little or no oxygen enrichment without any indication of equipment failure. It is presently unknown how many patients have died prematurely as a result of this type of equipment failure.

Another issue of growing significance is the misuse of oxygen, whether too little is delivered to the patient, as discussed above, or whether too much oxygen is being delivered to the patient. Ordinarily, one thinks of oxygen as a very beneficial although benign gas so that "the more oxygen the patient received, the better." Unfortunately, there is a certain class of respiratory care patient for whom extra oxygen is a lethal gas so that it is urgent for the attending physician to be able to accurately monitor the oxygen delivered to a patient, particularly a patient at a remote location.

Other examples of medical equipment which should be subjected to precision monitoring are items such as intravenous pumps, feeding pump systems, and pain suppression systems such as automatic or patient controlled morphine delivery systems. Importantly, any of the foregoing systems are susceptible of abuse either directly by the patient or indirectly by others in the vicinity of the patient.

DETAILED DESCRIPTION

Figure 2:
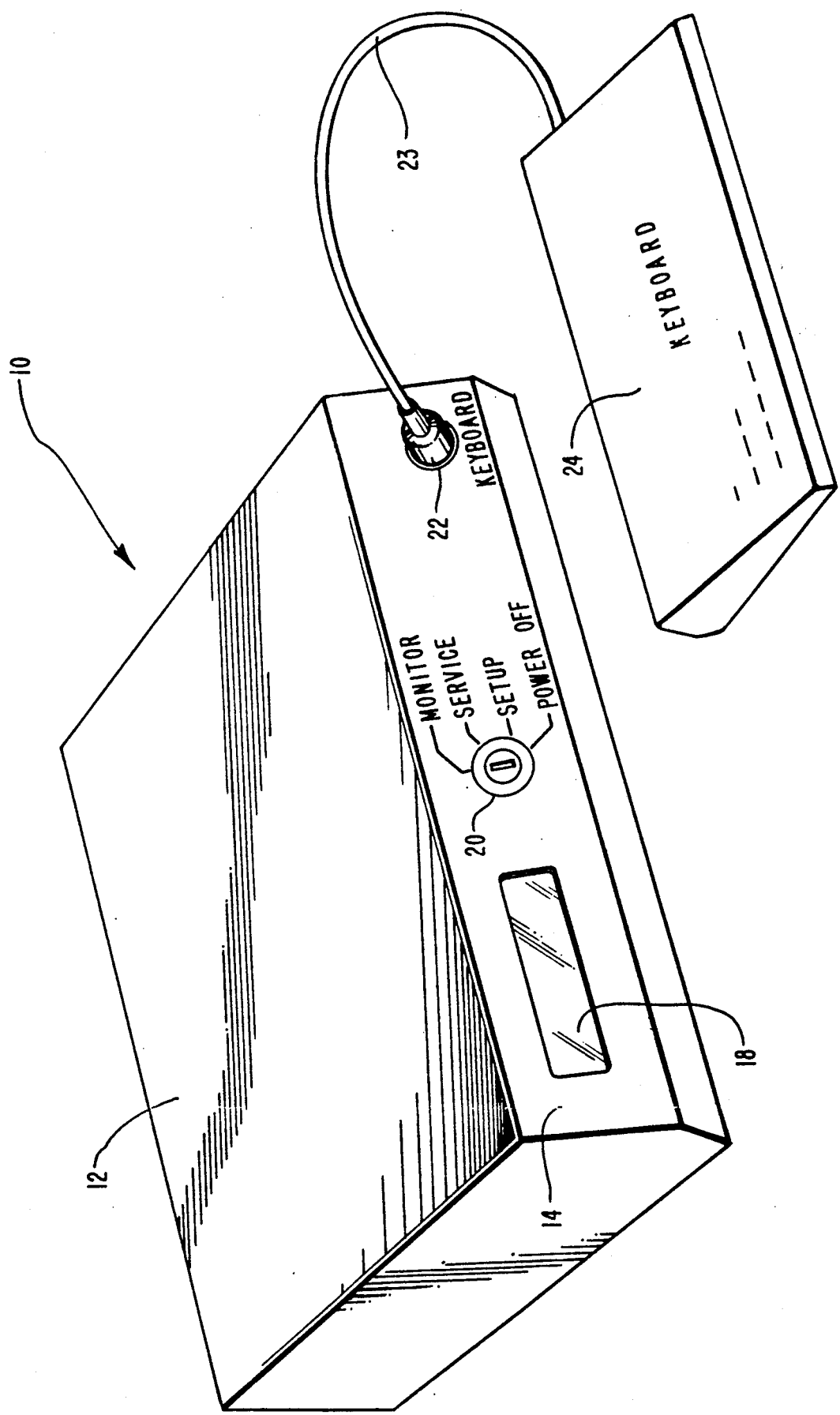
FIG. 2 is a perspective view of the monitor of FIG. 1 shown in the environment of a keyboard which is used for entering programming data into the monitor.
Figure 3:
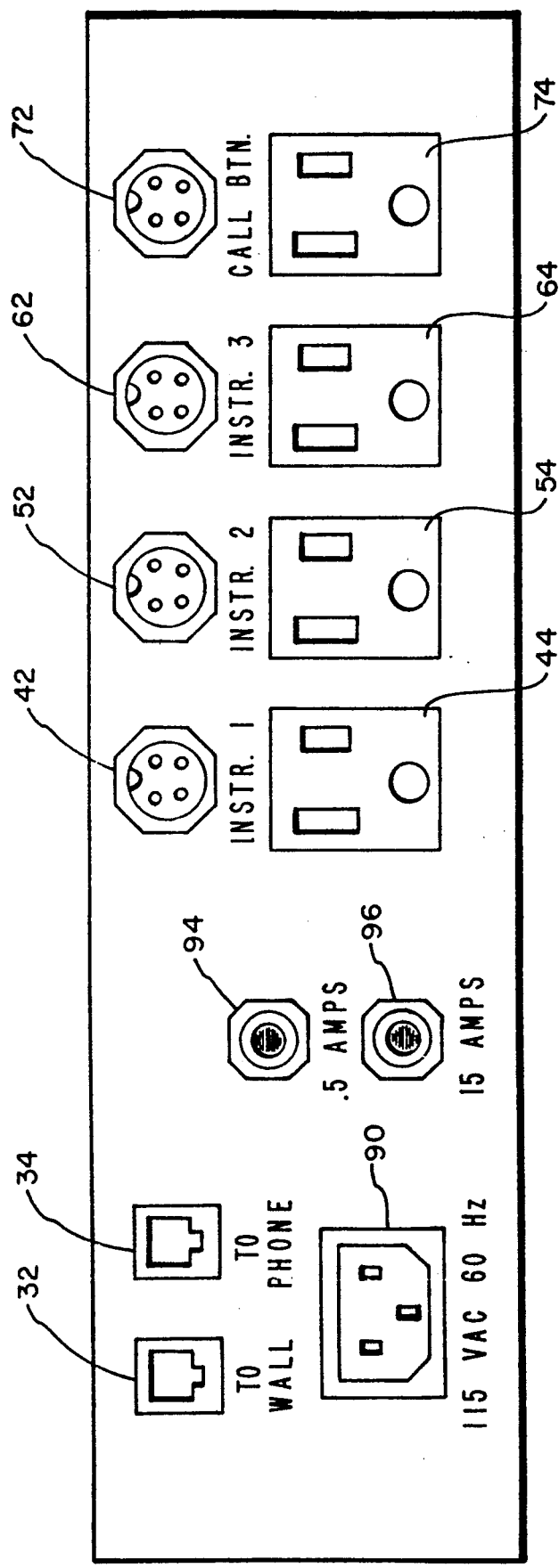
FIG. 3 is a plan view of the rear panel of the monitor of FIG. 2.

Referring now specifically to FIG. 2, the novel monitor apparatus of this invention is shown generally at 10 and includes a housing 12 with a front face 14 and a rear face 16 (FIG. 3). Front face 14 includes a liquid crystal display (LCD) 18, a selector switch 20 and a keyboard port 22 for a keyboard 24. A cord 23 connects keyboard 24 to keyboard port 22. LCD 18 is designed to provide a visual readout of the particular conditions being monitored by monitor 10 as selected by selector switch 20.

Selector switch 20 includes several settings such as Power Off; Set Up; Service; and Monitor. The Power Off setting is self-explanatory. The Set Up position is the mode whereby keyboard 24 is connected to keyboard port 22 by cord 23 to enable the operator (not shown) to enter the necessary data for the specific equipment being monitored by monitor 10. The internal program in monitor 10 cooperates through LCD 18 to visually provide the necessary instructions for the appropriate operation of keyboard 24. Keyboard 24 may also be used during the Service phase selected by selector switch 20 so that the desired equipment can be serviced.

Once the predetermined parameters are programmed into monitor 10 through keyboard 24 in the Set Up mode, selector switch 20 is turned to the Monitor position. Monitor 10 thereafter automatically monitors the selected medical equipment according to the predetermined parameters entered into its memory. Importantly, selector switch 20 is key-actuated by a specific key (not shown) so that only the person having possession of the specific key can alter or otherwise obtain access to monitor 10.

Referring now also to FIGS. 3 and 1, the layout of a presently preferred embodiment of rear face 16 is shown. Telephone jacks 32 and 34 interconnect monitor 10 between a telephone 30 and the household telephone jack (not shown), respectively. A male receptacle 90 receives electrical power through a power cord 92 from a conventional wall outlet (not shown). An internal buss (not shown) distributes electrical power to each of female receptacles 44, 54, 64, and 74, the function of each of which will be discussed more fully hereinafter. A pair of fuses 94 and 96 provide the necessary protection to the electronic components (not shown) inside monitor 10.

With specific reference to FIG. 1, monitor 10 is shown in the environment of a patient, indicated schematically at 80, resting on a bed 84. An oxygen source 40 supplies oxygen to patient 80 through a diffuser 48 fed by an oxygen line 46. The apparatus of oxygen source 40 and diffuser 48 is any suitable apparatus for delivering oxygen to patient 80 so that the actual equipment shown is merely illustrative. Clearly, any suitable oxygen delivery apparatus can be used for oxygen source 40.

Monitor 10 is coupled to oxygen source 40 through a monitor cord 42, and a power cord 43 each of which are connected to monitor 10 through receptacles 42 and 44, respectively, (FIG. 3). Electrical energy for oxygen source 40 is supplied through power cord 43, as described above, while monitor cord 42 directs monitoring signals form oxygen source 40 into monitor 10.

Similarly, a second item of medical equipment, in this instance a pulse oximeter 50, is coupled to monitor 10 by a monitor cord 53 interconnected at receptacle 52 (FIG. 3) and by a power cord 55 plugged into electrical receptacle 54. In this manner the operational characteristics of pulse oximeter 50 are continuously monitored by monitor 10. Pulse oximeter 50 a conventional pulse oximeter and has a sensing element 39 coupled to an ear 52 on patient 80. A cord 56 electrically interconnects sensing element 58 to pulse oximeter 50 so that the signals sensed by sensing element 58 are received by pulse oximeter 50.

A similar arrangement exists for a third item of medical equipment which is shown herein as an apnea monitor 60. Apnea monitor 60 is coupled to monitor 10 by a monitor code 63 which is plugged into receptacle 62 (FIG. 3) to enable monitor 10 to receive signals from apnea monitor 60. Power for apnea monitor 60 is delivered through a power cord 65 from an electrical receptacle 64. The sensing element (not shown) for apnea monitor 60 is coupled to patient 80 with the signals therefrom being delivered to apnea monitor 60 through cord 66.

It is important to note that all suitable items of medical equipment, whether oxygen source 40, pulse oximeter 50, or apnea monitor 60, or for that matter, any other similar item of medical equipment, each has a built in alarm system to which monitor 10 is electronically coupled. This means that monitor 10 uses the existing alarm/operational parameter system of each respective item of medical equipment to provide the necessary input to monitor 10. Accordingly, monitor 10 requires only a simple modification, if any, to adapt it to be able to suitably monitor the respective medical equipment.

A further item of convenience is a call button 70 coupled to receptacle 72 (FIG. 3) by a cord 73. Call button 70 can be selectively used by patient 80 to summon persons who can provide assistance to patient 80.

An additional receptacle 74 (FIG. 3) is provided on monitor 10 for the purpose of providing electrical power to any other selected item of equipment (not shown). This feature eliminates the need for additional wall outlets (not shown) for the purpose of supplying electrical power to a lamp, or other item requiring electrical power (not shown).

Figure 4:
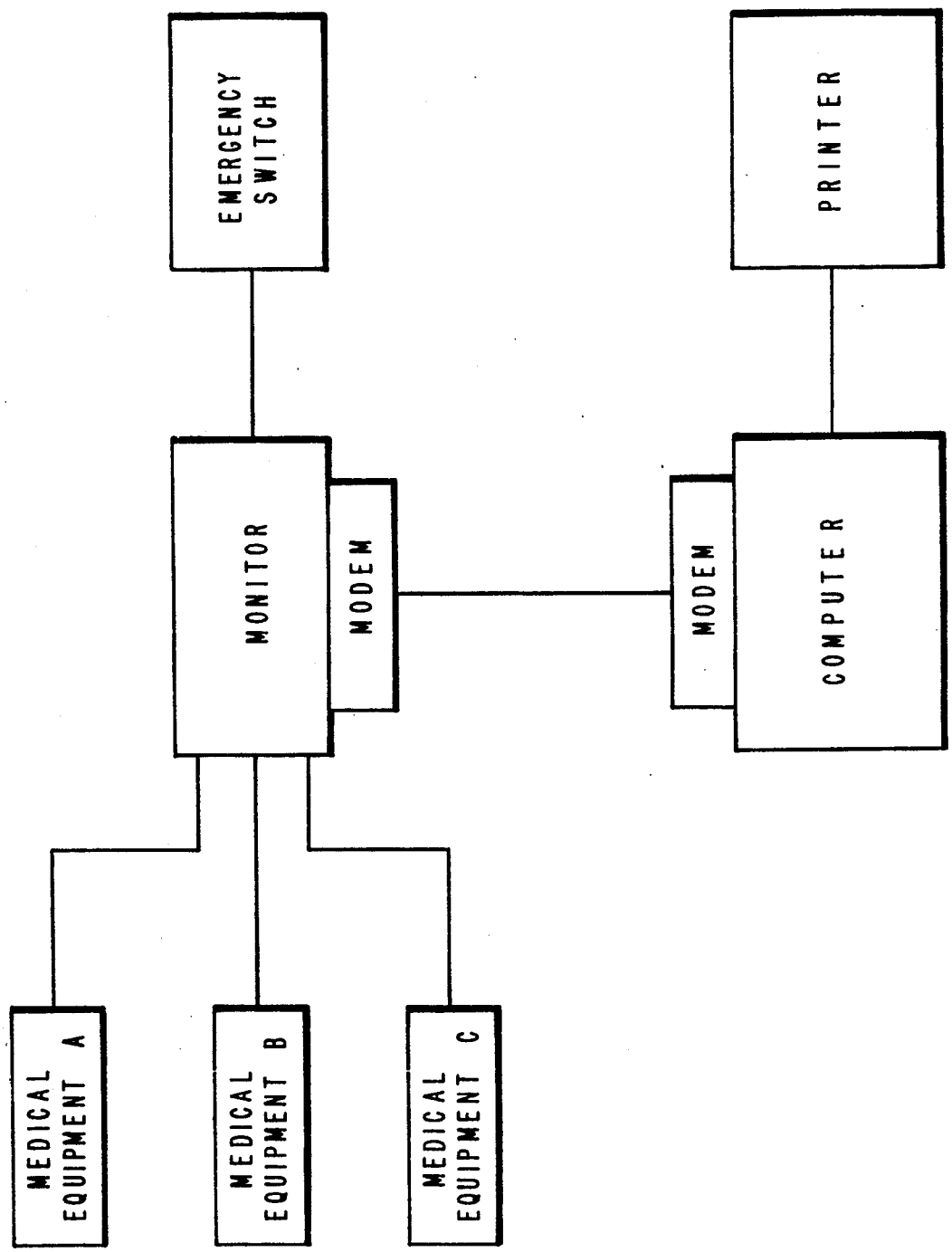
FIG. 4 is a schematic of the monitor connected to three items of medical equipment and linked by a telephone line to a computer at a remote location.

Referring now to FIG. 4, the schematic for a first, preferred embodiment of this invention is shown wherein a Monitor represents monitor 10 (FIGS. 1 and 2) and is coupled to Medical Equipment A (oxygen source 20, FIG. 1); Medical Equipment B (Pulse oximeter 50, FIG. 1); and Medical Equipment C (apnea monitor 60, FIG. 1). An Emergency Switch is coupled to the Monitor to illustrate the alarm feature of the Monitor although, clearly, the Emergency Switch is contained inside monitor 10 (FIGS. 1 and 2). The Monitor provides full twenty-four hour monitoring capability for up to three items of medical equipment in additional to the manual alarm capability provided by call button 70.

Operationally, when an alarm condition is detected by the monitor, an automatical call is made with the attached Modem through telephone 30 (FIG. 1), to the centrally located Computer and its attached Modem. This Computer is programmable to provide any desired form of response to signals received from the Monitor and has the capability to transmit instructions to an attached Printer which will print any desired amount of information. This Computer is on line all the time so as to be ready to receive incoming calls from the Monitor. Importantly, the Computer will respond to all incoming telephone messages by correctly identifying the Monitor and displaying the alarm condition. Further, from time to time the Computer will interrogate the Monitor for all information stored in the Monitor so that the information contained therein can be printed and stored in the patient's (patent 80, FIG. 1) file folder.

Monitor 10 is also programmed to dial the Computer through telephone 30 and can recognize when telephone line 33 is busy. Importantly, monitor 10 will continue dial the Computer at 15–30 second intervals until connection with the Computer. After connection has been made and all messages have been sent by monitor 10 to the Computer, monitor 10 will disconnect from telephone line 33 and continue to monitor according to its regular monitoring program.

Monitor 10 includes a battery (not shown) as a power failure safety device. This enables monitor 10 to alert the Computer to the emergency condition so that appropriate corrective measures can be implemented. Importantly, monitor 10 is programmed to wait thirty seconds prior to initiating this alarm in case the power failure is only a momentary interruption of electrical service.

Figure 5:
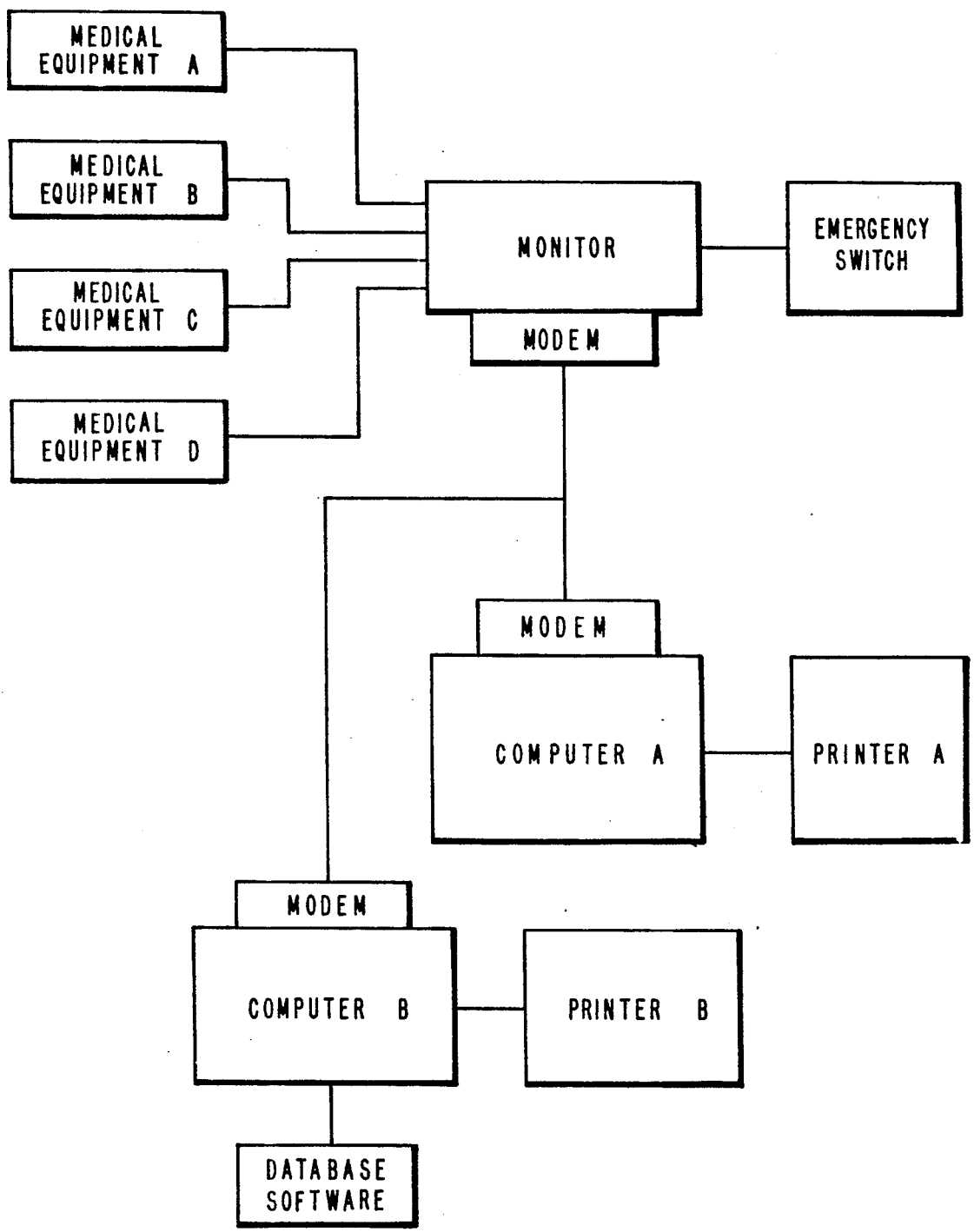
FIG. 5 is a schematic of the monitor connected to four items of medical equipment and linked by telephone lines to a first computer at a remote location and a second computer having a database.

Referring now to FIG. 5, a second preferred embodiment for the assembly of equipment around the Monitor (monitor 10, FIGS. 1 and 2) is shown in addition to its interconnection to other base station equipment as will be described more fully hereinafter. The Monitor is shown coupled to four items of medical equipment which are shown as Medical Equipment A, B, C, and D and can include any suitable medical equipment as discussed hereinbefore. In addition to being coupled to a base station computer system, shown herein as Computer A and Printer A, the Monitor can also be connected to a second computer system which is shown herein as Computer B, Printer B, and a Database Software. The Database Software includes such basic information as general client information and any other useful information that may be required. The Database Software is also set up in a spreadsheet format so that each parameter from the preselected medical equipment will in its own column. The Database Software is designed to enable Computer B to interrogate the Monitor on a daily basis in order to update the Database Software with the latest information.

Figure 6:
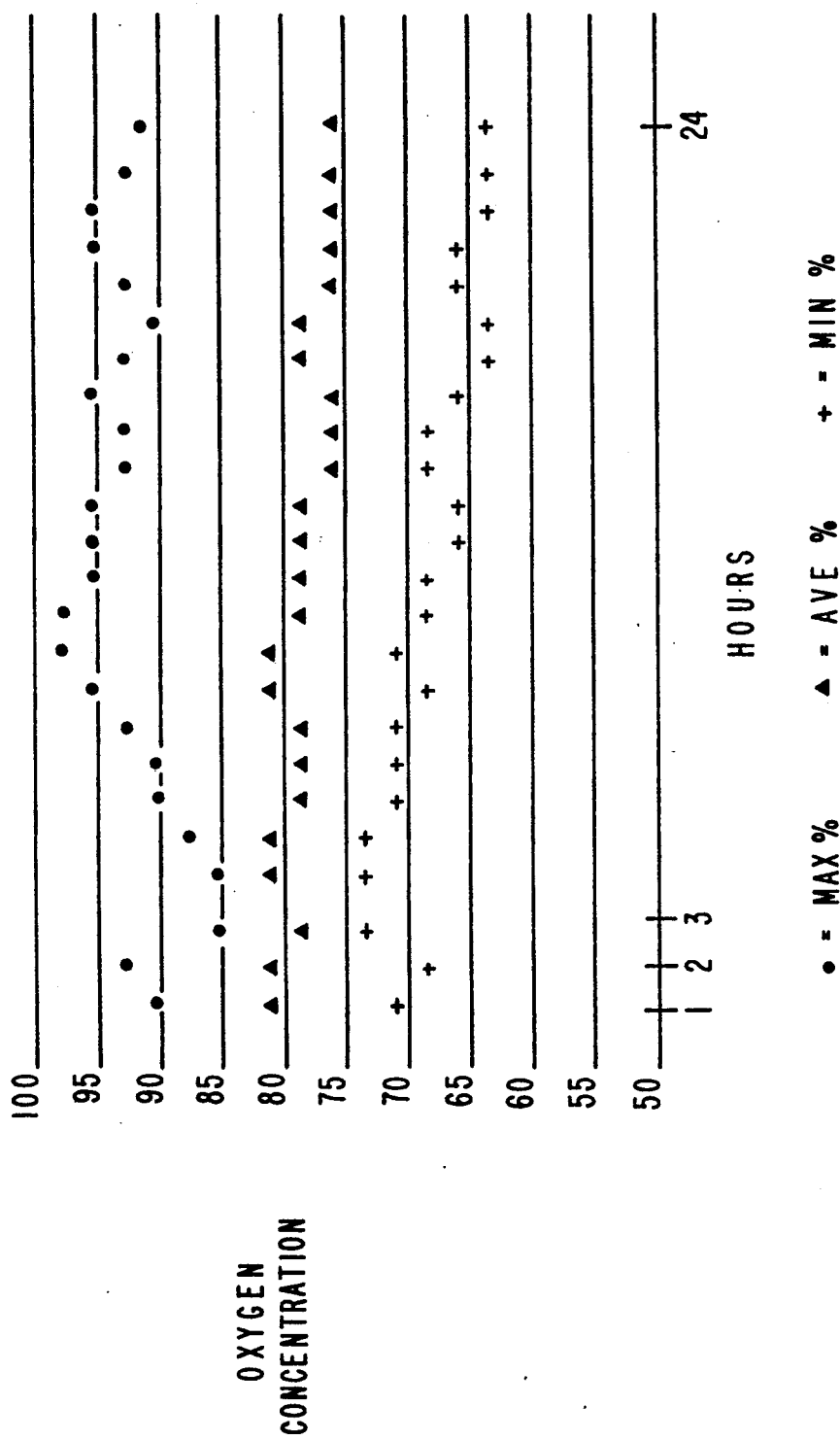
FIG. 6 is a chart showing the monitored parameters of oxygen concentration over a twenty-four hour period.

The daily information obtained by Computer B includes such information as the minimum, maximum, and average readings for each item of medical equipment on an hourly basis. Once the data has been entered into the Database Software, a line graph can be produced through Printer B. For example, FIG. 6 represents such a line graph for the maximum, minimum and average oxygen concentration delivered by oxygen supply 40 (FIG. 1) over a twenty-four hour period.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A monitor system for medical equipment comprising:
   one or more items of medical equipment, said medical equipment being located at a first location and including built-in electronic equipment operation deviation alarm systems;
   a monitor means interconnected with said medical equipment for receiving signals from said electronic equipment operation deviation alarm systems;
   transmission means in said monitor means for transmitting said electronic equipment operation deviation alarm signals over a telephone line to a second location; and
   recording means in said monitor means for recording information from said medical equipment.

2. The monitor system defined in claim 1 wherein said monitor means includes alarm means for producing an alarm when an alarm signal is received from said electronic equipment operation deviation alarm systems in said medical equipment.

3. The monitor system defined in claim 2 wherein said transmission means includes automatic redialing means for repeatedly redialing said second location over said telephone line in the event a busy signal is detected on said telephone line.

4. The monitor system defined in claim 1 wherein said monitor means includes an electrical power supply means for supplying electrical power to said medical equipment thereby enabling said monitor to detect when electrical power to said medical equipment is interrupted.

5. The monitor system defined in claim 1 wherein said transmission means includes means for transmitting said information recorded by said monitor from said medical equipment.

6. The monitor system defined in claim 1 wherein said monitor means includes a manual alarm that is operable by a patient being serviced by said medical equipment.

7. The monitor system defined in claim 1 wherein said monitor system includes a first base computer means for receiving and storing information from said monitor means.

8. The monitor system defined in claim 7 wherein said base computer means includes a first printer for printing said information.

9. The monitor system defined in claim 7 wherein said first base computer means includes a second computer and a database software for manipulating said information into a preselected format.

10. A medical equipment monitor system for monitoring selected parameters from a plurality of items of medical equipment, each item of medical equipment having an electronic signal means for producing electronic signals for signaling predetermined parameters and equipment operation deviation alarm conditions of said medical equipment comprising:
    a monitor having an electrical power receptacle for receiving electrical power from a source of electrical power and distribution outlets for distributing electrical power to said items of medical equipment, said monitor also including monitor means for monitoring said electronic signals and equipment operation deviation alarm conditions and transmission means for transmitting said equipment operation deviation alarm conditions to a second location, and recording means for recording said electronic signals and equipment operation deviation alarm conditions.

11. The monitor system defined in claim 10 wherein said transmission means includes automatic redialing means for repeatedly redialing said second location over said telephone line in the event a busy signal is detected on said telephone line.

12. The monitor system defined in claim 10 wherein said monitor includes a manual alarm that is operable by a patient being serviced by said medical equipment.

13. The monitor system defined in claim 10 wherein said monitor includes a first base computer means for receiving and storing information from said monitor means.

14. The monitor system defined in claim 13 wherein said first base computer means includes a first printer for printing said information.

15. The monitor system defined in claim 13 wherein said first base computer means includes a second computer and a database software for manipulating said information into a preselected format.

16. A method for monitoring electronic signals and equipment operation deviation alarm conditions from medical equipment comprising:
    obtaining a monitor, said monitor being capable of receiving, recording, and transmitting said electronic signals and said alarm conditions from said medical equipment;
    interfacing said monitor between said medical equipment and an electrical power source for said medical equipment;
    coupling the monitor capability of said monitor to said medical equipment thereby adapting the monitor for receiving said electronic signals and said alarm conditions;
    recording said electronic signals and said alarm conditions; and
    transmitting said alarm conditions.

17. The method defined in claim 16 wherein said obtaining step includes selecting a computer and interconnecting said monitor to said computer through a telephone line and said recording step includes directing said electronic signals and said alarm conditions to said computer.

18. The method defined in claim 17 wherein said interconnecting step includes redialing said computer in the event said monitor encounters a busy signal.

* * * * *